United States Patent [19]

Monno et al.

[11] Patent Number: 4,695,729
[45] Date of Patent: Sep. 22, 1987

[54] TUBULAR PART WALL THICKNESS MEASURING DEVICE

[75] Inventors: Asao Monno, Kanagawa; Kiyoo Watanabe; Kazuyuki Kaneko, both of Tokyo, all of Japan

[73] Assignees: Fuji Electric Co., Ltd.; Fuji Facom Corporation and Kawasaki Steel Corporation, both of Japan

[21] Appl. No.: 868,895

[22] Filed: May 27, 1986

Related U.S. Application Data

[63] Continuation of Ser. No. 515,230, Jul. 19, 1983.

[51] Int. Cl.⁴ ............................................. G01N 23/08
[52] U.S. Cl. ............................. 250/358.1; 250/359.1; 378/59
[58] Field of Search ............................ 378/54, 59, 56; 250/358.1, 359.1

[56] References Cited

U.S. PATENT DOCUMENTS

| | | | |
|---|---|---|---|
| 2,859,349 | 11/1958 | Bradley et al. | 378/59 |
| 3,278,747 | 10/1966 | Ohmart | 378/54 |
| 3,474,160 | 10/1969 | Doering | 250/360.1 |
| 3,489,901 | 1/1970 | Brown | 250/358.1 |
| 3,808,437 | 4/1974 | Miyagawa et al. | 378/54 |
| 4,088,886 | 5/1978 | Moulton | 378/56 |
| 4,182,954 | 1/1980 | Giles | 378/54 |
| 4,542,297 | 9/1985 | Hold | 250/359.1 |

FOREIGN PATENT DOCUMENTS

2440274 12/1977 Fed. Rep. of Germany .

Primary Examiner—Carolyn E. Fields
Attorney, Agent, or Firm—Sughrue, Mion, Zinn, Macpeak and Seas

[57] ABSTRACT

A tubular part wall thickness measuring device includes a radiation source having a plurality of radiation sources disposed in a line. The radiation passes through a collimator to provide parallel radiation beams which pass transversely through a tubular part to a radiation detector. The length of the radiation source and the radiation detector are greater than the diameter of the tubular part to be measured so that the radiation passes through an entire section of the tubular part so that the average wall thickness of the tubular part can be determined from the amount of attenuation of radiation which is detected by the detector.

1 Claim, 15 Drawing Figures

TUBULAR PART WALL THICKNESS MEASURING DEVICE

This is a continuation, of application Ser. No. 515,230, filed 7-19-83.

BACKGROUND OF THE INVENTION

The present invention is directed to a tubular part wall thickness measuring device and more specifically to a device utilizing a radiation source and detector having a length larger than the outside diameter of the tubular part being measured whereby parallel radiation beams emitted from the radiation source go through the detector at least through the entire section of the tubular part so that the average wall thickness of the tubular part can be determined from the amount of attenuation of radiation which is detected by the detector.

In general, in the manufacture of tubular pipes by conventional rolling operation in the steel industry the wall thickness of the tubular pipe must be measured with a high degree of accuracy. In order to increase productivity, it is essential to measure the wall thickness of the pipe on-line without stopping the flow of products. Furthermore, since the rolling operations generally involve a hot rolling step at very high temperatures, it is desireable that the wall thickness of the pipe be measured not only in a non-contact manner, but be measured at a distance as far as possible from the tubular part.

The arrangement of a conventional tubular part wall thickness measuring device is shown in FIG. 1 wherein $\gamma$-ray sources 1, 2, and 3 emit radiation which is detected by radiation detecting units or sensors 4, 5, and 6. The $\gamma$-ray sources 1 and 2 and the sensors 4 and 5 are mounted on a stationary frame 7 and the $\gamma$-ray source 3 and sensor 6 are mounted on a moveable frame 8. The tubular part 11, whose wall thickness is to be measured, is conveyed along a conveyor 9 in a direction transverse to the direction of the $\gamma$-rays.

In this operation the relative positions of the $\gamma$-ray sources and the sensors are important factors. The moveable frame 8 should be positioned in FIG. 1 so that the vertices of the regular triangle EFG, as shown in FIG. 2, which is formed by the beams, are on the circumference of a circle whose diameter is the mean value of the nominal outside and inside diameters of the tubular part 11 (hereinafter referred to as "a middle diameter"). The principle of measurement will not be described in the present application, since it has been disclosed in the specification of Japanese Patent Application Laid Open No. 46406/1981 and is not essential for understanding of the present invention.

As the tubular part 11 moves along the conveyor 9, the tubular part 11 is vibrated in the direction of the axes $Z_1$–$Z_2$ and $Z_3$–$Z_4$ as shown in FIG. 2, at all times. Accordingly, even if a vibration preventing roller (not shown) is added to the conveyor rollers 9, it is extremely difficult to precisely set the vertices of the regular triangle EFG formed by the three beams on the circumference of the circle having the middle diameter. Additional means, such as a vibration preventing roller, include very technical and very costly problems. The conventional measuring device as shown in FIGS. 1 and 2 suffers from the drawback that its measurement theoretically includes an error due to vibration which is referred to as a "mis-alignment error". Accordingly, the utilization of a vibration preventing roller in conjunction with a conveying roller 9 to minimize the vibration of the tubular part 11 to minimize alignment error, has not been widely practised.

Another method of measuring the wall thickness of a steel pipe by means of radiation is disclosed in Japanese Patent Application Laid Open No. 114263/1979. In the conventional method, based on the fact that radiation applied to a steel pipe from outside is attenuated to the maximum when passed tangentially of the inner surface of the pipe and is attenuated to a minimum when passed tangentially of the outer surface of the pipe, each the maximum and minimum attentuation points are detected so that the wall thickness of the pipe can be determined from the distance between both.

However, when a steel pipe having a wall thickness of 5 or 6 mm to 40 mm is measured according to the foregoing method, even if the radiation source employs a radioactive material of 30 curies, it takes at least 20 ms to 1 second for measurement because the amount of radiation from the radioactive source is generally fractured. Therefore, during this period, the steel pipe must be held at rest. Accordingly, such a method cannot be used in measuring on-line the wall thickness of steel pipe which is vibrated while being conveyed. Furthermore, it can be understood that where the image of a radiation projected steel pipe is taken with a television camera with the width of a slit for projecting radiation from the radiation source set at about 2 mm, the steel pipe wall thickness measurement accuracy according to the method is much lower than that of steel plate thickness gauge, several tens of micrometers, because the resolution of the television camera is only about 1 mm.

SUMMARY OF THE INVENTION

The present invention provides a new and improved tubular part wall thickness measuring device which is capable of achieving a high degree of accuracy even if the tubular part being conveyed undergoes vibration since no mis-alignment error is theoretically included in the wall thickness measurement.

. The present invention provides a new and improved tubular part wall thickness measuring device comprising a radiation source and detector which are arranged in such a manner as to confront each other with the tubular part to be measured disposed therebetwen, said radiation source and detector having a length larger than the outside diameter of the tubular part being measured whereby parallel radiation means emitted from said radiation source reaching the detector pass through the entire section of the tubular part so that the average wall thickness of the tubular part is determined from the amount of radiation attenuation which is determined by the detector.

The foregoing and other objects, features and advantages of the invention will be apparent from the following particular description of a preferred embodiment of the invention as illustrated in the accompanying drawings.

DETAILED DESCRIPTION OF THE INVENTION

Figure 1:
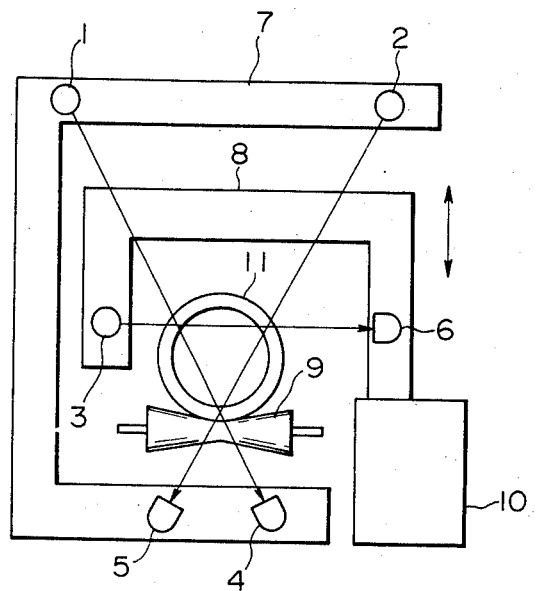
FIG. 1 is a schematic view showing a conventional measuring arrangement for measuring the wall thickness of a tubular part.
Figure 2:
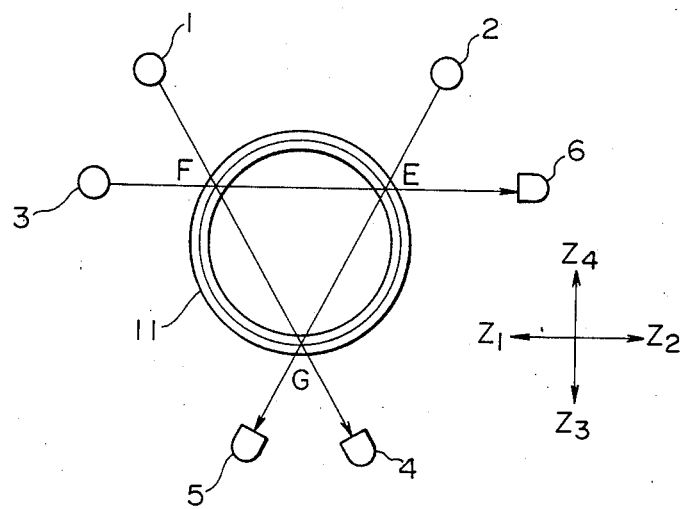
FIG. 2 is a schematic view showing a detail of the measuring arrangement of FIG. 1.
Figure 3A:
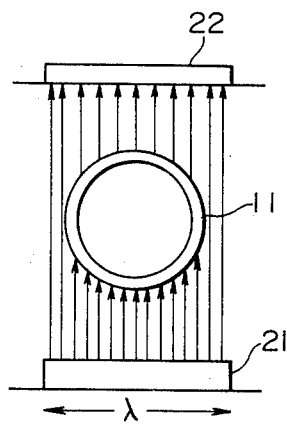
FIGS. 3a and 3b are explanatory diagrams with respect to the principle of a wall thickness measuring device according to the present invention.
Figure 3B:
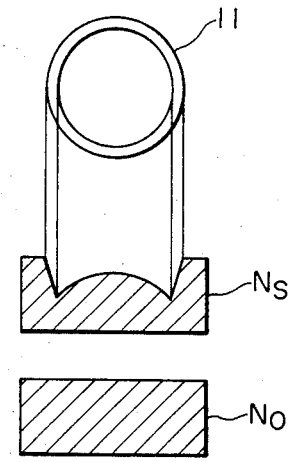

In order to understand the measurement principle according to the present invention, reference is made to FIGS. 3a and 3b. As seen in FIG. 3a, an array of γ-ray sources, referred to as a line radiation source 21 and an assembly of sensors arranged in a line and referred to as line sensor 22, are located on opposite sides of a tubular part 11. The length λ of the line radiation source 21 and the line sensor 22 is set to a value which is much larger than the outside diameter of the pipe 11 and the amount of attenuation of γ-rays from the source 21 is measured by the sensor 22 so that an average wall thickness of the pipe 11 in the section can be obtained. As illustrated in FIG. 3b, the total value of radiation detected by the line sensor 22 is designated by the reference character $N_o$ which is achieved when no pipe is present between the radiation source 21 and the sensor 22. The total count value of radiation is represented by the reference character $N_s$ which is detected when the pipe 11 is interposed between the source 21 and the sensor 22. The average wall thickness of the pipe 11 can be obtained from the two values $N_o$ and $N_s$. When the length λ of the line radiation source 21 and the line sensor 22 is much larger than the outside diameter of the pipe 11, even when the pipe 11 is vibrated, the total count values are not changed. Thus, according to the present invention, the average wall thickness of the pipe can be measured without any misalignment error.

Figure 4A:
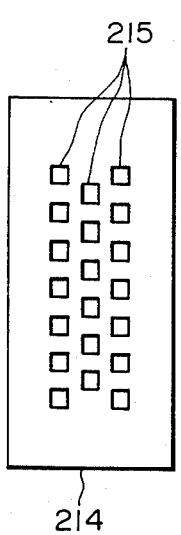
FIG. 4a is a sectional view showing the arrangement of one example of a line radiation source.
Figure 4B:
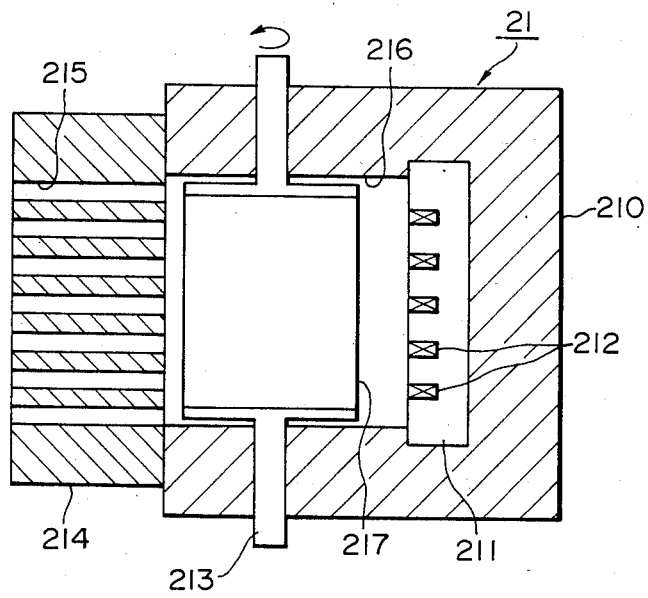
FIG. 4b is a front view of a collimator.

The line radiation source 21 may be formed as shown in FIG. 4a. A radiation source holder 211 is set in a line source container having a recess 216. A plurality of radiation source capsules 212, for instance, of cesium 137, are arranged in a line within the radiation source holder 211. A rotary shutter 213 is arranged in the recess 216 of the container 210. The container 210 is coupled to a collimator 214 which has a number of collimator holes 215 arranged in a plurality of lines, with the collimator holes of the adjacent ones of the lines being formed in a staggered relationship. The shutter 213 is turned by a rotating mechanism (not shown) in such a manner that the shutter plate 217 is held in parallel to the surface of the drawing to allow radiation from the capsules 212 to pass to the collimator 214 during a measurement and is held perpendicular to the surface of the drawing to block out the radiation when a measurement is not being carried out. The radiation is emitted radially from the capsules 212, but is converted through the collimator holes 215 of the collimator 214 into parallel radiation beams.

Figure 5A:
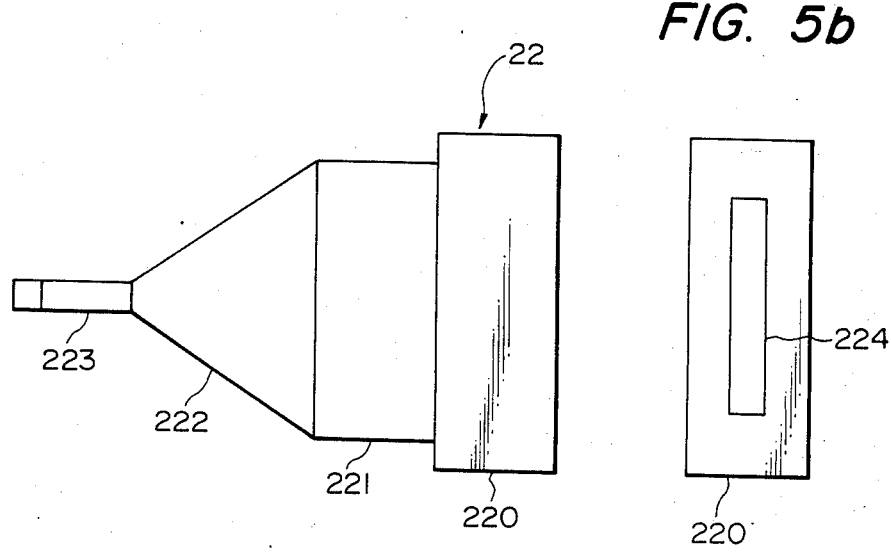
FIG. 5a is a side elevation view of a line sensor and FIG. 5b is a front view of a collimator used with the line sensor.
Figure 5B:

The line sensor 22 is shown in FIGS. 5a and 5b. A collimator 220 has a rectangular collimator hole 224 and a plastic scintillator 221 of polyvinyl toluene which is provided behind the collimator 220. A light guide 222 of acrylic is connected to the plastic scintillator 221. A photo-multiplier tube, 223, is coupled to light guide 222 and the output of the tube 223 is applied to an amplifier (not shown). Radiation from the line radiation source 21 is formed into parallel beams by the collimator holes 215 of collimator 214 as described above. The parallel beams, after passing through the pipe, enter the collimator hole 224 in the collimator 220 of the line sensor. A Collimator hole 224 is a single rectangular hole, but may be replaced by a number of collimator holes which are arranged in lines similar to the collimator holes 215 in the line radiation source 221.

It is well known that the following fundamental equation is established for a radiation transmission-type thickness gauge:

$$N = N_0 \text{EXP}(-\mu t) \quad (1)$$

where N is the detection output of the sensor when the radiation passes through an object having a thickness t, $N_0$ is the detection output or reference output of the sensor when no object is provided (when the thickness t equals 0), and μ is a constant or absorption coefficient.

Figure 6:
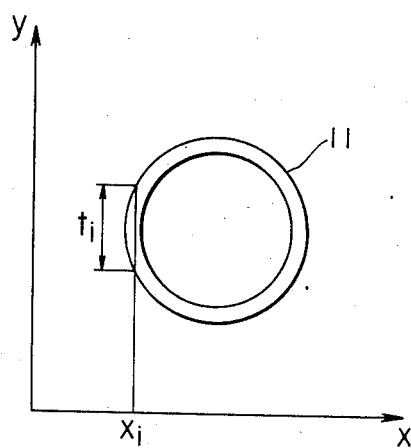
FIG. 6 is an explanatory diagram for describing the functional relationship between the wall thickness of a pipe and its position.

As shown in FIG. 6, an x-axis and a y-axis are disposed relative to a section of pipe 11 in such a manner that the axes are perpendicular to each other. Thus, a wall thickness $t_i$ of the pipe 11 in the direction of the y-axis can be expressed as a function of the x-distance $x_i$ as follows:

$$t_i = f(x) \quad (2)$$

therefore, the detection output $N_s$ of the line sensor 22 as shown in FIG. 3a is as follows:

$$N_s = \int_0^l N_0 \text{EXP}(-\mu F(X)) \, dx \quad (3)$$

Figure 7:
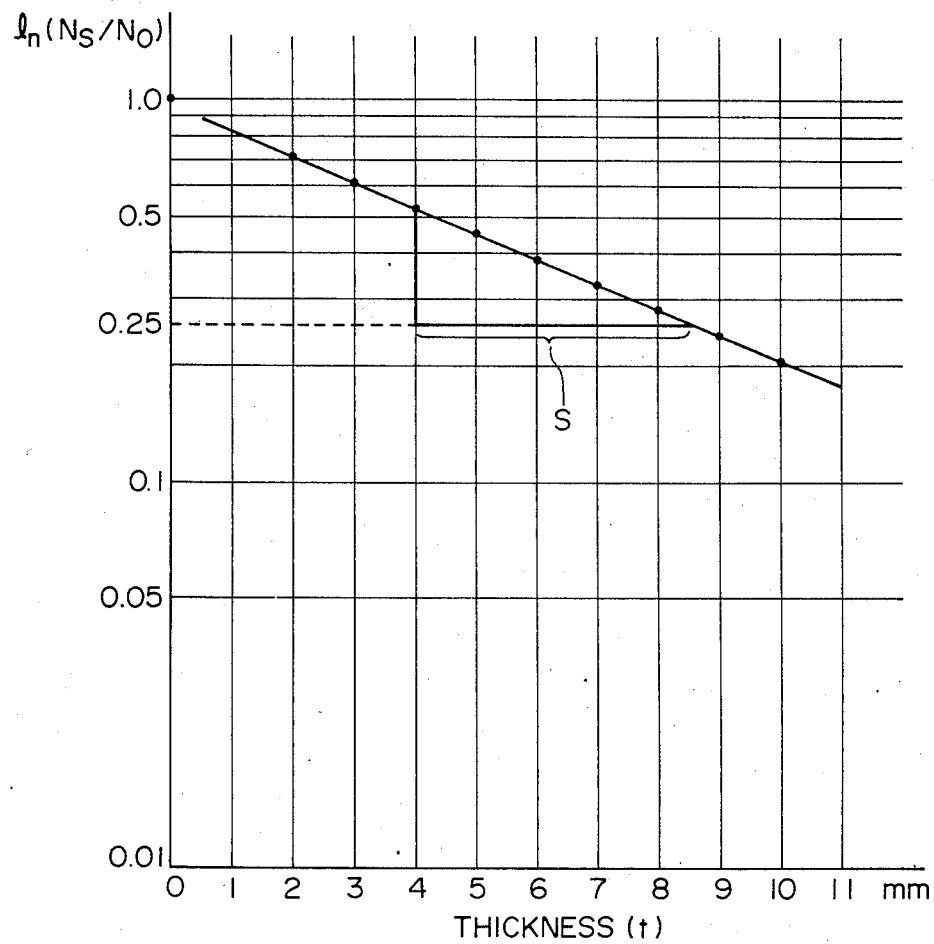
FIG. 7 is a graphical representation indicating wall thicknesses with radiation detection elements of the sensor.

FIG. 7 is a graphical representation indicating the wall thickness t at various x-distances with detection outputs $N_s$ therefor.

As is apparent from FIG. 7, when a value $l_n(N_s/N_0)$ on the y-axis is decreased to half, the amount S of change in wall thickness (hereinafter referred to as "a half value layer") it is about 4.5 mm.

In general, if the half value layer is excessively large or small, the measurement becomes difficult. A half value layer for an ordinary flat plate which is measured by a transmission-type thickness gauge, which is extensively employed, is about 11 mm. As the aforementioned value 4.5 mm is about a half ($\frac{1}{2}$) of this value (11 mm), the tubular part wall thickness measuring device according to the above-described principle has a measurement accuracy which can be expected to be substantially the same as that of the above-disclosed gauge.

As is apparent from FIG. 7, the attentuation characteristic curve is linear in the wall thickness range from 3 mm to 15 mm (about 0.03 to 0.1 in the ratio (t/d) of wall thickness (S) to diameter (D)) and correction, which is required when the curve is non-linear, is unnecessary; that is, the average wall thickness of a tubular part can be determined directly from the detection output of the line sensor.

Figure 8:
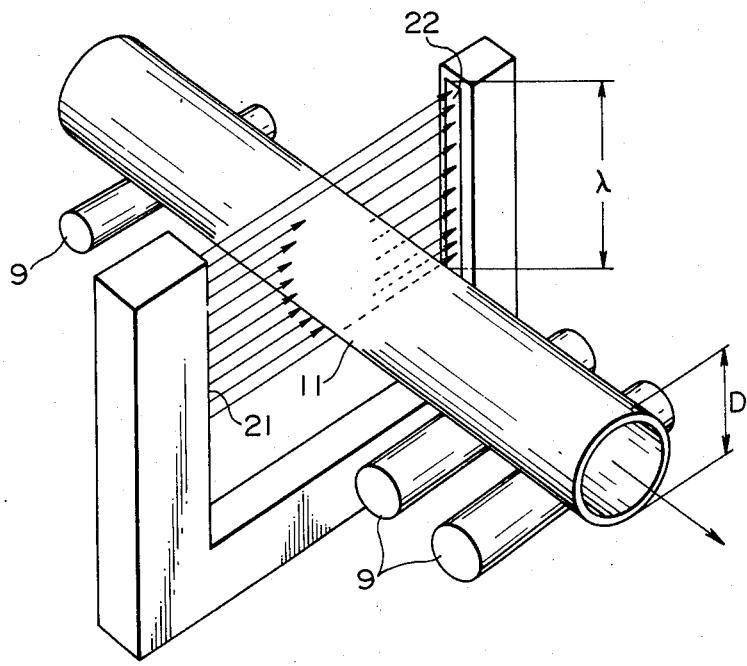
FIG. 8 is a perspective schematic view showing an example of a tubular part wall thickness measuring device according to the present invention.

Using the measurement principle described above, a tubular part wall measuring device as shown in FIG. 8 can be used to determine the wall thickness of a tubular part. The rollers 9 are provided to convey the tubular part 11 transversely of the measuring device. The length λ of a line radiation source 21 and a line sensor 22, is set to a value much higher than the outside diameter D of the pipe 11. Such a measuring device a high speed response type wall thickness measuring device which can measure the wall thickness of a pipe in a non-contact manner while the pipe is online irrespective of the vibration of the pipe which is caused as the pipe is being conveyed. The wall thickness thus measured can be fed back to the work piece rolling means to facilitate the control of speed or temperature therein to thereby contribute to the quality control of the pipe.

In the system according to the present invention, the half value layer is about one-half of that of a flat plate as previously described. This means that the variation in the quantity of radiation which is caused when a flat plate changes by 1 mm in thickness is equal to that in the quantity of radiation which is caused when a tubular pipe changes about 0.5 mm in thickness. Accordingly, the wall thickness of a pipe can be measured at least as finely as the thickness of a flat plate so that the degree of accuracy is very high.

Figure 9A:
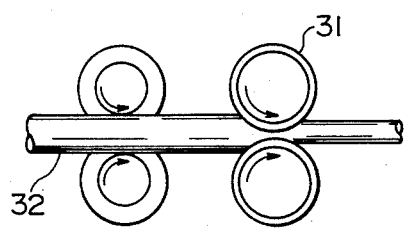
FIGS. 9a and 9b are side and front views, respectively, of a two roll reducer.
Figure 9B:
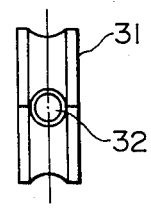
Figure 10A:
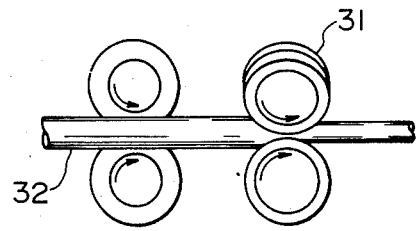
FIG. 10a and 10b are side and front views, respectively, of a three roll reducer.
Figure 10B:
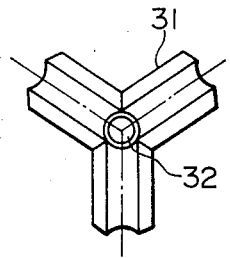

The tubular part wall thickness measuring device according to the present invention is especially suitable for use with a stretch reducer. A stretch reducer is a mill which is used in the finishing rolling operation and is used in almost all the final finishing operations for small diameter seam pipes. It is also used in the finishing process for small diameter welded pipes because of its high degree of efficiency. In the stretch reducer, fourteen to twenty roll housings having two and three rolls are arranged successively along a pipe, and while the outside diameter of the pipe is being rolled, the rolls of adjacent stands are made different in peripheral speeds so that the pipe is pulled longitudinally while being rolled and the wall thickness is controlled. Accordingly, if several kinds of pipes are provided then a variety of pipes different in diameter can be formed. A two roll reducer is shown in FIGS. 9a and 9b, while a three roll reducer is shown in FIGS. 10a and 10b. In these figures the rolls 31 are shown in conjunction with a pipe 32 which is being pulled. With such a stretch reducer, the wall thickness of a pipe is changed by pulling it in the longitudinal direction. Therefore, in order to improve the control for operation of the mill, it is essential to detect the average wall thickness of a pipe in the longitudinal direction rather than to detect an irregularity in wall thickness in the section of the pipe, especially in the case of a welded steel pipe which is manufactured from plate material having a uniform thickness.

In the case where the speed of a multi-stage mill is changed to change the tension exerted on the pipe to control its wall thickness, it is preferable that the response speed of the wall thickness measuring device is high. When the wall thickness measuring device is applied to the stretch reducer it is generally located at the input or output side so that the pipe will be exposed to a considerable amount of vibration. However, there is no room for vibration-preventing pinch rollers in these locations. Accordingly, the advantages of the present invention are that the measurements are not affected by the vibration of the pipe and the response speed of the device is very high.

While the average wall thickness in the pipe section can be measured by the prior art devices, the prior art devices are extremely expensive since at least three radiation sources and three detectors are required. On the other hand, the device according to the present invention has only a single radiation source and a single detector and therefore can be manufactured at much lower cost.

While the invention has been described with reference to a steel pipe, it should be noted that the technical concept of the present invention is extensively applicable to the measurement of the wall thickness of generally tubular pipes by using gamma rays, x-rays, beta-rays, ultra-violet rays, visible rays or infra-red rays separately, according to the pipe material such as metal, plastic, glass, cement, etc.

While the invention has been particularly shown and described with reference to a preferred embodiment thereof, it will be understood by those in the art that the foregoing and other changes in form and details may be made therein without departing from the spirit and scope of the invention.

What is claimed is:

1. A device for measuring the wall thickness of a tubular part, comprising:
   radiation source means;
   radiation detector means disposed in spaced apart aligned relation with respect to said source means, to accommodate a tubular part therebetween, the length of said detector means being at least as large as the length of said radiation source means, and a width of a radiation beam from said radiation source means being substantially larger than a diameter of said tubular part, said tubular part comprising a continuously or intermittently vibrating element, and said radiation source means and said radiation detector means providing a gap therebetween, said gap having a length in a transverse direction larger than said diameter of said tubular part in said transverse direction, and
   wherein said radiation source means and said radiation detector means are each provided with collimator means having at least one opening for providing parallel radiation beams, a width of a radiation beam provided by said source means and said collimator means of said source means being sufficiently larger than said diameter of said tubular part to allow for vibration of said part, said collimator means of said source means being provided with an opening defined by a plurality of collimator holes arranged in a plurality of lines, the collimator holes of adjacent ones of said lines being formed in a staggered relationship; and
   a transverse gap defined by said source means, said detector means, said collimator means of said source means, and said collimator means of said detector means having a length sufficiently larger than said diameter of said tubular part to allow for vibration in said transverse direction; the length of said detector means being at least larger than the length of said opening of said detector collimator means; and
   wherein said radiation detector means provides an output for determining an average wall thickness of said tubular parts.

* * * * *